US009429551B2

(12) United States Patent
Podgorney

(10) Patent No.: US 9,429,551 B2
(45) Date of Patent: Aug. 30, 2016

(54) GENERATION OF CARBON MONOXIDE FOR TESTING SENSORS AND DETECTORS

(75) Inventor: Harvey Podgorney, Luton (GB)

(73) Assignee: SATA LIMITED, Hertfordshire (GB)

(*) Notice: Subject to any disclaimer, the term of this patent is extended or adjusted under 35 U.S.C. 154(b) by 1295 days.

(21) Appl. No.: 11/997,200

(22) PCT Filed: Jul. 18, 2006

(86) PCT No.: PCT/GB2006/002671
§ 371 (c)(1),
(2), (4) Date: Jul. 31, 2008

(87) PCT Pub. No.: WO2007/015054
PCT Pub. Date: Feb. 8, 2007

(65) Prior Publication Data
US 2009/0311165 A1   Dec. 17, 2009

(30) Foreign Application Priority Data
Aug. 1, 2005  (GB) .................................. 0515816.7

(51) Int. Cl.
*G01N 33/00* (2006.01)
*C01B 31/18* (2006.01)

(52) U.S. Cl.
CPC ........... *G01N 33/0006* (2013.01); *C01B 31/18* (2013.01); *G01N 33/004* (2013.01)

(58) Field of Classification Search
CPC ............. G01N 33/004; G01N 33/007; G01N 2033/0072; G01N 33/0063
USPC .......................... 204/173; 73/1.06, 1.03, 1.02
See application file for complete search history.

(56) References Cited

U.S. PATENT DOCUMENTS

| 4,271,693 | A  | * | 6/1981  | Bute ............................. 73/1.03 |
| 5,069,765 | A  | * | 12/1991 | Lewis ........................... 204/173 |
| 6,225,733 | B1 | * | 5/2001  | Gadkaree et al. ............ 313/352 |
| 6,282,940 | B1 | * | 9/2001  | Hung et al. ................... 73/1.06 |
| 7,212,734 | B2 | * | 5/2007  | Pepper et al. ................ 392/379 |

FOREIGN PATENT DOCUMENTS

DE        3721671 C1      7/1988

OTHER PUBLICATIONS

Written Opinion and Search Report of International Application No. PCT/GB2006/002671 mailed Oct. 27, 2006.
(Publication 6) Utility Model Application No. S55-133911 (Utility Model Application Publication No. S67-060297) microfilm.
Japanese Patent Application Publication No. S63-106100.
Utility Model Application No. S61-065236 (Utility Model Application Publication No. S62-179698) microfilm.
Office Action for corresponding Chinese Application No. 200680028248.2; dated Feb. 11, 2011.
(Continued)

*Primary Examiner* — Sally Merkling
(74) *Attorney, Agent, or Firm* — Koppel, Patrick, Heybl & Philpott

(57) ABSTRACT

A method and apparatus for generating carbon monoxide and in particular a device for testing carbon monoxide detectors which utilizes the method and apparatus for generating carbon monoxide. A layer of Activated Carbon Cloth is heated so that it produces small quantities of carbon monoxide. The Activated Carbon Cloth may be provided in a removable cassette.

16 Claims, 2 Drawing Sheets

(56) References Cited

OTHER PUBLICATIONS

English translation of Office Action for corresponding Chinese Application No. 200680028248.2.
Wu Mingbo, et al, "Study on Pore Structure and Absorption Property of the Activated Carbon Felt Prepared by Using CO2 as Activating Agent", *New Carbon Materials*, vol. 14, No. 2, pp. 54-58, Jun. 30, 1999.
Examination Report for corresponding Japanese Application No. 306495; dated May 23, 2010, & English translation.
(Publication 1) Japanese Patent Application Publication No. S58-055321; & English abstract.
(Publication 2) Japanese Patent Application Publication No. 2001-508532; & English equivalent PCT patent publication.
(Publication 3) Japanese Patent Application Publication No. 2005-511295; & English equivalent PCT patent publication.
(Publication 4) Japanese Patent Application Publication No. H11-287460.
(Publication 5) Utility Model Application No. S62-074377 (Utility Model Application Publication No. S63-183693) microfilm.

* cited by examiner

GENERATION OF CARBON MONOXIDE FOR TESTING SENSORS AND DETECTORS

The present invention relates to a method and apparatus for generating carbon monoxide (CO) and in particular to a method and apparatus for the production of carbon monoxide gas for use in testing of carbon monoxide sensors, detectors and alarms.

BACKGROUND TO THE INVENTION

Carbon monoxide (CO) is a colourless, odourless, invisible, and very toxic gas. It is the product of incomplete combustion. If a carbon-based fuel, such as petrol, wood, coal or charcoal briquettes, is burned in an atmosphere with insufficient oxygen, the carbon in the fuel is not completely oxidised into carbon dioxide, and carbon monoxide results.

Hazard detectors and alarms which contain CO sensors are used in both the domestic and the industrial sectors. The CO sensors/detectors monitor the atmosphere for the presence of a build up of CO, which might be the consequence of a faulty gas heater or a slow-burning fire.

Over a period of time, the CO sensors deteriorate. In order to verify the performance of the sensor and the correct operation of any hazard detector or alarm containing a CO sensor, periodic tests need to be carried out on them. To perform such a test, a small amount of CO needs to be introduced into the sensor/detector in a concentration that is large enough to activate the sensor/detector into an alarm mode, but small enough, such that if it were released into the atmosphere, it would be within safe limits and pose no risk to human health.

Currently there are a variety of methods for testing CO sensors in hazard detectors. These include the use of small glass vials of CO which are broken in the presence of the sensor/detector, smouldering Incense Sticks or using a dilute mixture of carbon monoxide gas mixed with air, nitrogen or another inert gas. In the latter case, the gas is usually stored in a pressurised cylinder or in an aerosol can. One such CO aerosol can tester is sold under the trade name Solo CO™.

These methods are either not convenient, or are considered dangerous. The use of glass vials can be dangerous, as a new glass vial must be broken each time a test is carried out. Plus the CO contained in such vials is generally very concentrated and therefore poses a risk to human health. In the case of smouldering Incense Sticks, a naked flame must be used for ignition, a significant odour is produced and they do not lend themselves to applications where repeated tests are required throughout a prolonged working period. In addition, the use of pressurised containers is not convenient as they are often heavy and bulky and they are classified as hazardous, hence costly to transport. Since a large amount of the gas can be stored in larger containers, and the gas itself is odourless, it can be dangerous or even fatal if the contents are released in a confined unventilated space.

Other current methods for producing CO (usually on a commercial scale) are too large to be scaled down, and the production of CO by the chemical reaction of hazardous chemicals is deemed too dangerous to incorporate into a portable appliance.

It is an object of the present invention to address the above-identified problems and to provide a safe and easy to way to generate CO that can then be utilised in a sensor/detector tester.

It is a further object of the present invention to provide a portable CO sensor/detector tester.

It is a further object of the present invention to provide a CO sensor/detector tester which utilises non-hazardous materials and/or chemicals.

SUMMARY OF THE INVENTION

The present invention provides an apparatus for generating carbon monoxide, comprising: an activated charcoal layer; an electrical heating means arranged, in use, to heat said layer of activated charcoal whereby to produce carbon monoxide.

Preferably, the activated charcoal is provided in a removable cassette.

Preferably, the present invention provides an apparatus for testing a carbon monoxide sensor comprising the apparatus for generating carbon monoxide described above and a housing having a first chamber having an opening arranged to receive a device containing a carbon monoxide sensor, and a second chamber arranged to receive a removable activated charcoal layer cassette.

The present invention also provides the cassette for use in the above device, having a layer or ribbon of activated charcoal disposed therein. Preferably, the layer or ribbon of activated carbon is activated carbon cloth (ACC). ACC is a textile made from bundles of activated carbon fibres which are knitted or woven together. Activated Charcoal is also known as Active Charcoal, Activated Carbon and Active Carbon.

The present invention further provides a method of producing carbon monoxide for use in the testing of a carbon monoxide sensor, comprising the steps of: heating a layer of activated carbon so as to produce carbon monoxide; and directing said carbon monoxide to a carbon monoxide detector.

Preferably, the CO is generated in small quantities in a controlled and safe manner and passed into the detector under test.

Preferably, the device is electrically operated.

The layer of activated charcoal is a safe, inert source of CO, that does not burn or remain hot when heated by the device. Thus, the device does not use or store any harmful chemicals or dangerous gases (apart from the small amount of CO generated by the layer of activated charcoal). In addition, the present invention is easily transportable and avoids the disadvantages of the other methods and devices in that it offers a fail-safe solution in the event that one or more of the controlling components were to fail.

The present invention is based on the principle of heating ACC in a controlled manner, within an enclosure. When the temperature of the ACC reaches 80° C. CO generation begins in small quantities. Increasing the heat applied to the ACC, results in larger amounts of CO being produced (see FIG. 1). FIG. 1 shows a graph of ACC temperature 20 and CO output 21 against time. The horizontal axis shows time in seconds and the vertical axis shows both ACC temperature in degrees Celsius and CO quantities in parts per million.

One of the attributes of using layers of activated carbon or ACC is that it is extremely safe as it will not burn or retain heat. Unlike the heating of Activated Charcoal pellets, the application of too much heat in the presence of oxygen will not cause self-perpetuating burning of the ACC leading to an uncontrollable run away scenario. Instead, the ACC will just form a harmless ash, making this invention safe to use. Further protection is afforded in that the controlling electronics regulates the amount of CO released, and this can be reduced or totally constrained. Thus, the principle employed by the present invention does not involve the combustion of the activated charcoal in the conventional sense. Conventional combustion is a rapid chemical process which involves the production of heat and usually light. Rapid combustion of carbon may result in the production of carbon monoxide (which is a well known process) but this is different to the principle employed by the present invention, in which there is no combustion of this type. When ACC is heated, there is no self-sustaining combustion. Instead, the ACC decomposes under the effect of applied heat to release CO without conventional combustion. In this connection, the ACC does not continue to burn when the heat source is removed and does not produce heat or light.

Preferably, the amount of CO produced is controlled by using a CO sensor and control electronics.

The present invention preferably provides a device for testing carbon monoxide testers which is portable. Thus the device can be easily used and arranged in position for testing CO sensors/detectors.

The present invention preferably provides a device which utilises non-hazardous materials. Thus, the device does not present any risk to the user.

The present invention preferably provides a device which utilises materials which do not ignite when over-heated. Thus, in the event that the tape cassette containing the layer of activated charcoal becomes jammed and the same piece of activated carbon is heated repeatedly, the activated carbon does not ignite. Instead, it simply decomposes and disintegrates. In this manner, there is no risk to the user in the event of over-heating.

BRIEF DESCRIPTION OF THE DRAWINGS

So that the present invention may be more easily understood, embodiments thereof will now be described by way of example only and with reference to the accompanying drawings, in which.

DESCRIPTION OF THE PREFERRED EMBODIMENTS OF THE INVENTION

The preferred embodiment of the present invention relates to apparatus for generating carbon monoxide (CO) in a manner and in sufficient quantities to be useful in a number of different areas. In particular, the apparatus is suitable for use in portable apparatus for testing any piece of equipment, such as an alarm, which contains a CO sensor or detector.

Figure 1:
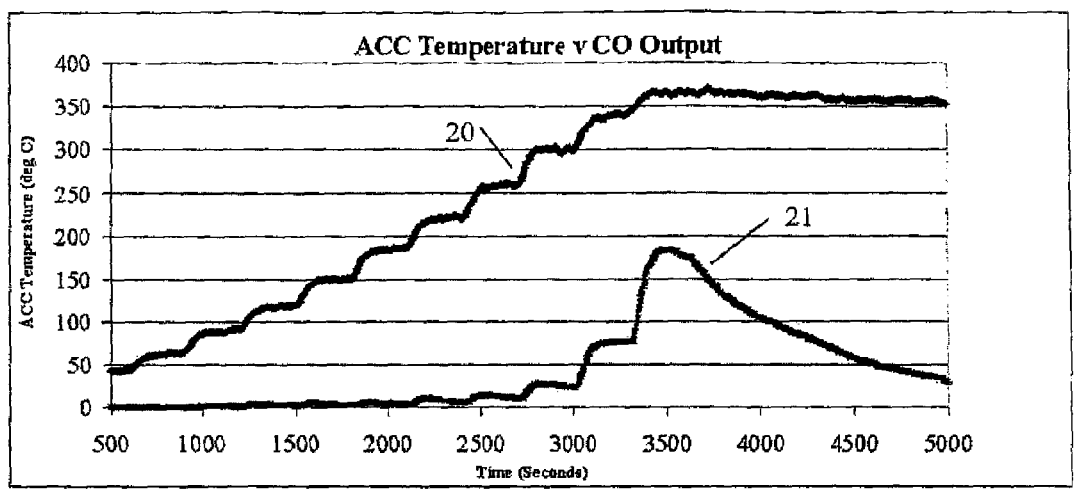
FIG. 1 is a graph showing CO output vs. temperature for Activated Charcoal Cloth.
Figure 2:
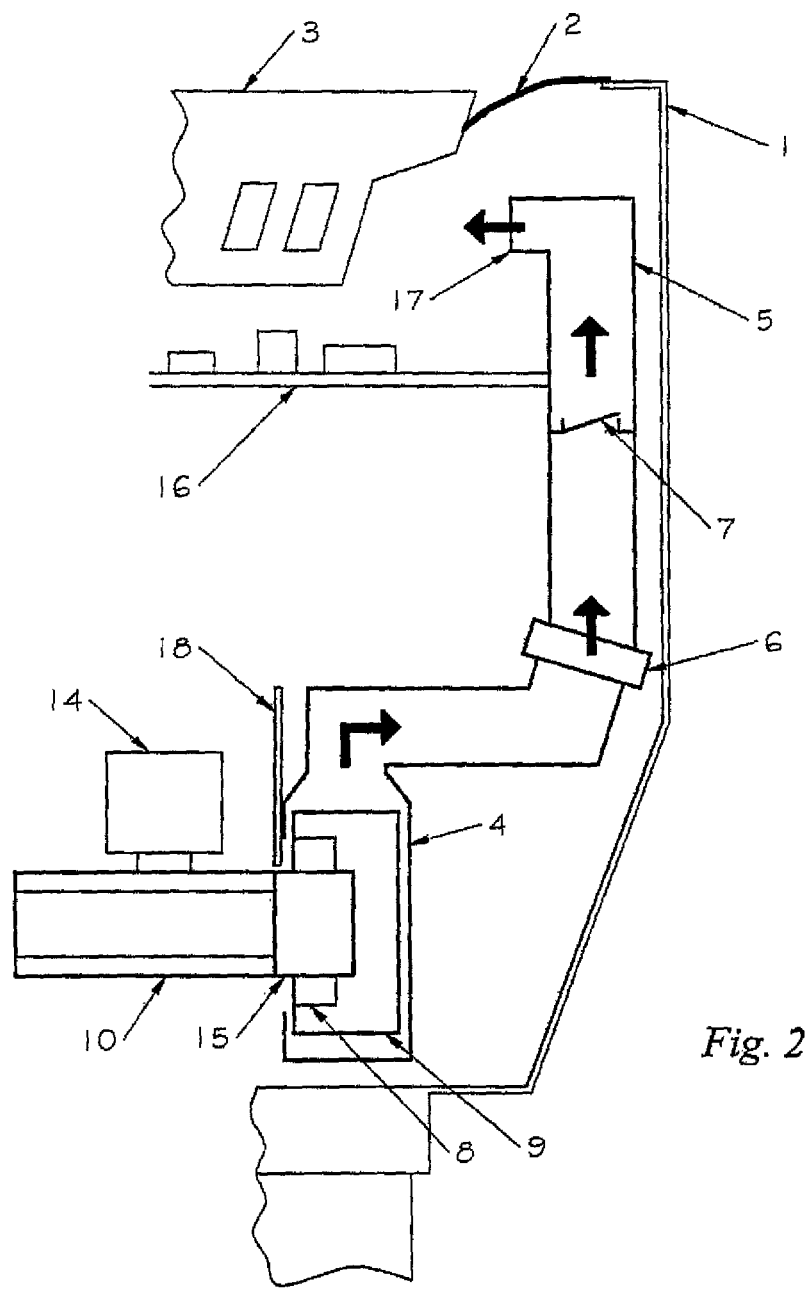
FIG. 2 is a cross-sectional side view of a preferred embodiment of the present invention.

Referring first to FIG. 2 which shows a cross-sectional side view of the CO sensor/detector tester. The CO sensor/detector tester includes a cup shaped housing 1 with a flexible membrane 2 that can accommodate the sensor/detector 3 under test. The size and shape of the cup shaped housing should be appropriate to accommodate the internal components of the tester. The opening in the top of the cup shaped housing can also be varied in size and shape as necessary to accommodate any type of CO sensor/detector. The membrane can be arranged such that one size and shape of tester can be used with a variety of CO sensor/detectors.

The CO generator is located in the collection chamber 4, which resides in the lower part of the cup shaped housing 1. It is connected to the upper portion by means of a delivery duct 5 containing a lift fan 6 and an optional regulator valve 7, which has a horizontal outlet 17 to direct the gas across the sensor/detector 3.

The CO generator comprises an electrically operated heater assembly 8, mounted in a heat resistant retainer 9 and a cassette mechanism 10 (shown in more detail in FIG. 3) containing a length of activated carbon cloth (ACC) in the form of a ribbon 11. The ACC is a textile made from bundles of activated carbon fibres which are joined together through for example knitting or weaving. Any type of joining technique can be used to create the textile material as long as there is interengagement between the activated carbon fibres to form the cloth.

The heater assembly comprises of a wire heating element 12, enclosed within a glass tube 13, which can be either silica or quartz glass. The cassette 10 connects to a motor 14, which moves the ACC ribbon 11 in defined increments to present a fresh length of ACC to the heater assembly 8 for each test. The generator resides within the collection chamber 4, which connects to the delivery duct 5.

Figure 3:
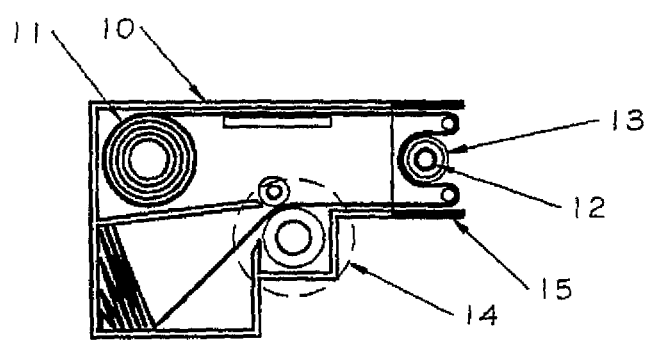
FIG. 3 is a cassette mechanism of the preferred embodiment of the present invention.

FIG. 3 shows the cassette mechanism of the present invention. The cassette mechanism has a heat resistant tip 15, that is located in the housing 1 such that the ACC ribbon 11 is brought into contact with the heater assembly. When in place, the ribbon is wrapped around the heating assembly 8. When the ribbon is exhausted along its entire length, a new cassette can be inserted. As a further safety precaution, a safety shutter 18 actuated by the cartridge, covers the opening to the element so that a user can not physically touch it, even when the cassette mechanism is removed.

The ACC ribbon 11 is brought into contact with the heating assembly 8, through which an electric current is passed in a controlled manner using a defined algorithm. This heat is transferred to the ACC ribbon 11 so that the quantity of CO gas generated can be controlled. The generated CO is gathered within the collection chamber 4 and by the action of the lift fan 6, in conjunction with the optional regulator valve 7, is transferred through the delivery duct 5 at a controlled rate and hence to the output 17. The flow of gas from the collection chamber 4 may be regulated by controlling the speed of the fan 6 and by the adjustment of the optional regulating valve 7. The inclusion of a CO sensor and a monitoring circuit within the tester would afford a more consistent control of the CO.

Control of the currents to the heating assembly, motor and the regulating valve are accomplished using control circuitry on a circuit board 16 designed to control the attributes of the CO generator.

Once the sensor/detector has gone into alarm, it may be necessary to clear the gas from the sensor/detector. This can be accomplished by turning off the CO generator and using the fan 6 to blow clean air over the sensor/detector.

The present invention has been described above in the context of a device which utilises a removable cassette containing the activated charcoal. However, as an alternative the activated charcoal may be loaded directly into the device without utilising a cassette. This would enable the possibility of the entire device being disposable. The device could be built with the activated charcoal preloaded and offering a certain number of tests. Once these tests have been completed, the device could be disposed of and a new device used. Alternatively, the activated charcoal could be replaced using means other than a cassette. For example, the activated charcoal ribbon, could be formed on a reel which could be directly loaded into the device.

The invention claimed is:

1. A portable testing apparatus for testing a carbon monoxide sensor by generating carbon monoxide, the apparatus comprising:
a housing;
a source of activated carbon comprising a layer of non-hazardous activated carbon cloth;
a carbon monoxide generator comprising an electrical heater assembly arranged, to heat a portion of the layer of non-hazardous activated carbon cloth to produce carbon monoxide;
a collection chamber contained within one part of said housing and arranged to collect carbon monoxide produced from heating the portion of activated carbon cloth layer; and
a delivery duct contained in the housing and connected to said collection chamber, said delivery duct arranged to direct the collected carbon monoxide from the collection chamber in said one part of said housing to another part of said housing and towards the carbon monoxide sensor in order to test the carbon monoxide sensor;
wherein the apparatus is hand-transportable; and
wherein said source of activated carbon is removable and replaceable.

2. The apparatus of claim 1 wherein said heating means comprises a heating element enclosed in a glass tube.

3. The apparatus of claim 1 wherein said activated carbon cloth layer is in the form of a ribbon.

4. The apparatus of claim 1 further comprising moving means for moving a portion of the layer of activated charcoal into the proximity of the heating means, whereby in use, said portion of the layer of activated carbon produces carbon monoxide.

5. The apparatus of claim 4 wherein said activated carbon cloth is provided in a removable cassette.

6. The apparatus of claim 5 further comprising a housing having a first chamber having an opening arranged to receive a device containing a carbon monoxide sensor, and a second chamber arranged to receive said removable activated carbon cloth cassette.

7. The apparatus of claim 6 wherein the moving means comprises a motor arranged to drive said cassette.

8. The apparatus of claim 6 wherein said delivery duct connects said first and second chambers.

9. The apparatus of claim 8, wherein said delivery duct comprises a fan arranged to, in use, move gas along the duct connecting the first and second chambers.

10. The apparatus of claim 8 wherein said delivery duct comprises a valve.

11. The apparatus of claim 6 further comprising a shutter arranged to cover said heating means when no cassette is positioned in the second chamber.

12. The apparatus of claim 1 further comprising a control circuit arranged to control the operation of the apparatus.

13. A cassette for use in the apparatus claimed in claim 1, having a ribbon of activated charcoal disposed therein.

14. The cassette of claim 13 comprising a heat resistant tip.

15. The cassette of claim 13 wherein said ribbon of activated charcoal is activated charcoal cloth.

16. The apparatus of claim 1, wherein said portion of activated carbon cloth layer is wrapped around the heating means.

* * * * *